United States Patent
Schulze et al.

(10) Patent No.: US 6,443,011 B1
(45) Date of Patent: Sep. 3, 2002

(54) DEVICE FOR DETECTING ERRORS AND/OR MEASURING WALL THICKNESS IN CONTINUOUS STRIPS OR TUBES MADE OF PLASTIC USING ULTRASONIC SIGNALS

(75) Inventors: Torsten Schulze, Bad Oeynhausen (DE); Reinhard Klose, Rinteln (DE)

(73) Assignee: INOEX GmbH, Bad Oeynhausen (DE)

( * ) Notice: Subject to any disclaimer, the term of this patent is extended or adjusted under 35 U.S.C. 154(b) by 0 days.

(21) Appl. No.: 09/554,774
(22) PCT Filed: Nov. 13, 1998
(86) PCT No.: PCT/EP98/07515
§ 371 (c)(1), (2), (4) Date: Jun. 24, 2000
(87) PCT Pub. No.: WO99/26040
PCT Pub. Date: May 27, 2000

(30) Foreign Application Priority Data

Nov. 19, 1997 (DE) .......................................... 197 51 193

(51) Int. Cl.[7] .............................................. G01N 29/10
(52) U.S. Cl. .............................. 73/622; 73/599; 73/600; 73/602; 73/592
(58) Field of Search .......................... 73/520, 592, 627, 73/628, 638, 620, 629, 632, 682, 624, 615, 599, 602, 600, 622

(56) References Cited

U.S. PATENT DOCUMENTS

| | | | |
|---|---|---|---|
| 4,679,437 A | * | 7/1987 | Koike et al. .................. 73/622 |
| 4,905,527 A | * | 3/1990 | Harth et al. ................ 73/865.8 |
| 5,085,082 A | * | 2/1992 | Cantor et al. .................. 73/622 |
| 5,460,046 A | | 10/1995 | Maltby et al. ................ 73/628 |
| 5,535,628 A | * | 7/1996 | Rutherford .................... 73/622 |
| 5,708,208 A | * | 1/1998 | Bonitz .......................... 73/628 |
| 5,992,235 A | * | 11/1999 | Fischer et al. ................ 73/628 |
| 6,070,832 A | * | 6/2000 | Redd ............................ 73/628 |
| 6,266,983 B1 | * | 7/2001 | Takada et al. ................ 72/11.1 |

FOREIGN PATENT DOCUMENTS

| | | | |
|---|---|---|---|
| DE | 28 06 550 A1 | 8/1979 | |
| DE | 28 52 768 A1 | 6/1980 | |
| JP | 60235055 | * 11/1985 | .................. 73/628 |
| JP | 05126803 | * 5/1993 | .................. 73/628 |

* cited by examiner

Primary Examiner—Hezron Williams
Assistant Examiner—Jacques Saint-Surin
(74) Attorney, Agent, or Firm—Dick and Harris

(57) ABSTRACT

The invention relates to a device for detecting faults in and/or measuring the wall thickness of continuously moving strips, sections or tubes of plastics, using ultrasonic signals. To this end a number of ultrasonic heads (A, B, C, D) with transmitters and receivers are disposed distributed over the width of the strip or section or the periphery of the tube. The signal, emitted by a transmitter of an ultrasonic measuring head (3) and reflected without scatter, is received by the receiver of said ultrasonic measuring head (3), while the scattered signals reflected on the tube, section or the like are received by the receivers of its adjacent ultrasonic measuring heads (A, B). The inclusion of the scattered and reflected signals in the measurement appreciably increases the measured area per measurement in comparison with using exclusively the signal directly reflected without scatter.

1 Claim, 4 Drawing Sheets

DEVICE FOR DETECTING ERRORS AND/OR MEASURING WALL THICKNESS IN CONTINUOUS STRIPS OR TUBES MADE OF PLASTIC USING ULTRASONIC SIGNALS

BACKGROUND OF THE INVENTION

The invention relates to a device for detecting faults and/or measuring the wall thickness of continuously moving strips, sections or tubes of plastics, using ultrasonic signals, which, for the complete coverage of the wall of the strip, section or tube, are introduced perpendicularly into the plastics from measuring heads distributed one beside the other and transversely of the direction in which the strip, section or tube runs, over the width of the strip or section or the periphery of the tube, and fixed above the strip, section or tube, their reflected signals being received by them and supplied to an evaluation unit.

In a known device of the kind specified (U.S. Pat. No. 4,740,146) for cylindrical tubes a few measuring heads are disposed fixed with a relatively large spacing around the tube, thus covering the tube wall at only a few strips extending in the direction in which the tubes move. Such a device for wall thickness measurement may, as a rule, be adequate since variations in thickness over the periphery are usually not limited to narrow longitudinal strips but extend over a fairly large peripheral area. However, if variations in thickness deviate from the rule, no fault-free wall thickness measurement is possible. Such a device is basically unsuitable for the detection of faults, since faults are frequently confined exclusively to a very small place.

However, the tube wall can be checked over its entire periphery using another known device (DE 40 33 443 A1) which has a measuring head extending over the entire periphery of the tube. However, driving and guiding such a measuring head involves considerable costs for machinery, and there is also the fact that such a measuring head can cover the continuously moving tube only over spiral paths. In this case also, therefore, there may be zones which are not covered.

To enable a tube to be covered over its entire surface, measuring heads might form a closed ring. However, one disadvantage of such a device is that it necessitates a large number of measuring heads.

To enable faults and their orientation to be detected in a tube wall, a device for fault detection is known (U.S. Pat. No. 4,523,468) which uses two groups of measuring heads disposed one behind the other on the external periphery of the tube to introduce ultrasonic signals into the tube wall and receive signals reflected at faults. To the end the first group generates signals which spread out axially in the tube wall, while the second group generates ultrasonic signals spreading out in the peripheral direction. Allowing for the position of the measuring head emitting an ultrasonic signal and the position of the measuring head receiving the reflected signal and also the propagation time, it is possible to determine the position of the fault in the tube wall. The position and orientation of the fault can be determined by a number of such measurements. To prevent the mixing of the ultrasonic signals emitted by the individual measuring heads in the receiving measuring heads, the measuring heads are so operated in succession by a multiplex method that a number of receiving measuring heads are associated with each measuring head emitting an ultrasonic signal.

The wall thickness of tubes and the like cannot be determined using such a device fault direction, in which the measuring heads of one group transmit exclusively axially ultrasonic signals, the other group of measuring heads extending exclusively peripherally of the tube and emitting ultrasonic signals. Since this device also involves exclusively the determination of relatively large faults and their orientation in the tube, the problem of covering the tube over its whole area using solely measuring heads operative in a relatively small zone plays no part.

It is an object of the invention to provide a device for the complete coverage of the wall thickness and/or faults in strips, sections or tubes with a convexly curved surface.

SUMMARY OF THE INVENTION

This problem is solved according to the invention in a device of the kind specified by the features that the measuring heads are so disposed one beside the other and transversely of the direction in which the strip, section or tube moves, allowing for the sonic propagation, scatter and refraction of the reflected signals on the strip, section or tube, that they completely cover the wall of the strip, section or tube, those signals of a signal emitted by the transmitter of each measuring head which are reflected on the strip, section or tube being received by said measuring head and by the measuring heads adjacent on each side thereof; while the number of measuring heads is $$N \geq \frac{\pi R}{S \tan \alpha}$$

The diameter of the receiving of each measuring head is $$K \geq \frac{2 \pi R}{NT}$$

And the wavelength of the ultrasonic signal is $$\lambda \geq R\, 1 - \cos \frac{360}{NT}$$

where
  N=number of measuring heads;
  R=external radius of curvature of the surface of the strip, section or tube;
  S=distance of the measuring head from the curved surface;
  α=opening angle of the ultrasonic transmitter of the measuring heads;
  K=diameter of the receiving surface of each measuring head and
  T=number of measuring zones per measuring head;
  λ=wavelength of the ultrasonic signal.

While in conventional devices for fault detection and/or wall thickness measurement using measuring heads operating by the ultrasonic pulse echo method, the receiver of a measuring head receives exclusively the signal emitted by the transmitter of said measuring head and reflected, but not the signals refracted at the curved surface and therefore "lost" to the measurement, according to the invention even these "lost" portions of the emitted and reflected ultrasonic signal are utilized for the measurement, said signals being received by the sensors of the adjacent measuring heads. This enables the entire surface of the object to be measured to be covered completely using a few ultrasonic measuring heads. Since as a result the signal emitted by an ultrasonic measuring head passes over a larger area, fewer measuring heads are required than in the conventional devices.

If the rules according to the invention for the design of the measuring heads are respected, telescoped bell-shaped curves for the sonic pressure of adjacent measuring heads are obtained for the ultrasonic signals emitted from the ultrasonic measuring heads and reflected on the tube or strip to be tested. Due to the design of the measuring heads, said bell-shaped curves must be telescoped in one another to such an extent that the sonic pressure for the evaluation of echo signals is still adequate as far as the intersection point of the bell-shaped curves. When determining the number of measuring zones per measuring heads, it must be remembered that measuring zones are partially "mirrored", since between two adjacent measuring heads the same measuring zone is first covered by the reflected signal emitted by one measuring head and received by the other adjacent measuring head, and then by the reflected signal transmitted from the other measuring head and received by an adjacent measuring head. Such "mirrored" measuring zones—i.e., zones covered twice, count only once.

It is basically possible for the surface to be covered without any overlapping, taking into account the unrefracted, reflected signals and the refracted, reflected signals. In that case, the smallest number of measuring heads per unit of area measured will suffice. Provision cannot however also be made for overlapping to take place, so that each portion is investigated not only using a reflected signal without refraction, but also using a refracted reflected signal. In the latter case there is the advantage that due to their different angle of incidence, the refracted signals can detect faults which can hardly be detected by an unrefracted signal.

To facilitate the processing of the signals, provision can be made that not all the signals are supplied in parallel to the valuation unit, but the measuring heads are operated cyclically. However, a number of cycles can run in parallel.

DETAILED DESCRIPTION OF THE DRAWINGS

Figure 1:
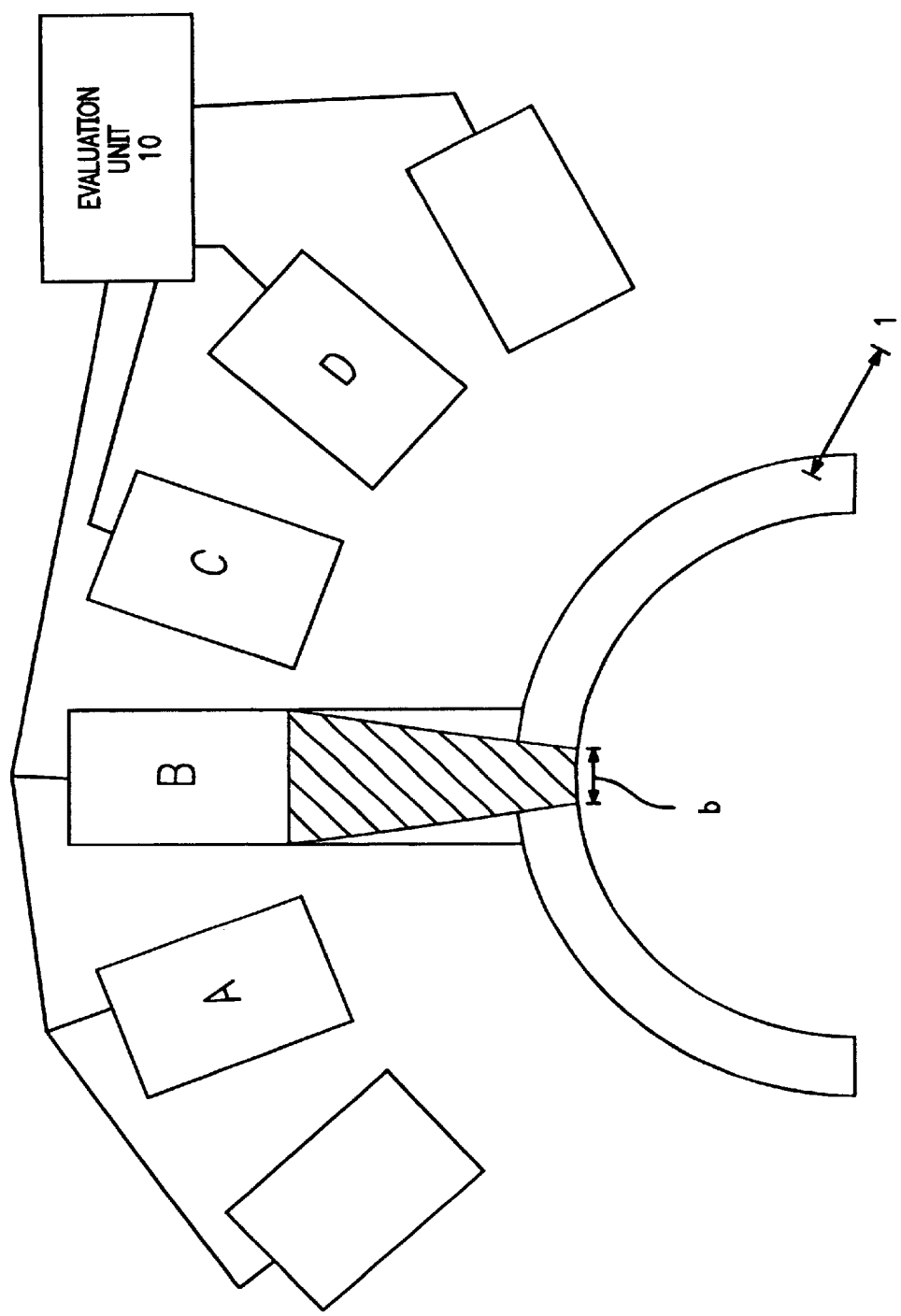
FIG. 1 is a schematic drawing showing a portion of a reflected ultrasonic signal emitted from measuring head B which is received by measuring head B, according to the invention.

The invention will now be explained in greater detail with reference to drawings illustrating an embodiment thereof. It must be remembered that the presentation can only be in the nature of a model, since the whole path of the rays of ultrasonic signals cannot be physically and actually represented in a drawing.

The invention comprises on the one hand measuring heads which are disposed in a particular geometrical relationship to the object to be measured, for example, a tube, and on the other hand the operating and evaluation unit 10. The operating unit so operates the measuring heads in cycles that one measuring head emits and receives the reflected signal, the two adjacent measuring heads only receiving. The evaluation unit 10 evaluates the reflected received signals having regard to the geometrical arrangement of the measuring heads, more particularly the natural drop in sonic pressure at the edges of the signal. The special kind of evaluation does not form part of the invention.

The drawings show the geometrical relationships of the complete coverage of a tube wall by means of measuring heads disposed one beside the other, having regard to the unscattered, reflected ultrasonic signals and the scattered reflected ultrasonic signals. The term "unscattered" means a reflection with refraction such that the signal emitted by the measuring head can also be received by said measuring head, while "scattered" means such a reflection with refraction that the signal emitted by the measuring head cannot be received by said measuring head but only by measuring heads disposed at its sides.

A number of ultrasonic measuring heads A, B, C, D are positioned spaced out in a circle around a cylindrical tube 1 (only half shown). The ultrasonic measuring heads A, B, C, D are directed perpendicularly at the tube 1 and disposed at a distance S from the surface of the tube. Each ultrasonic measuring head A, B, C, D emits ultrasonic signals which spread out conically and not without opening angle, as shown in the drawings for reasons of simplicity. A receiving surface having a diameter $K_s$ is available for receiving the entry and rear wall echo of the ultrasonic signals.

Figure 2:
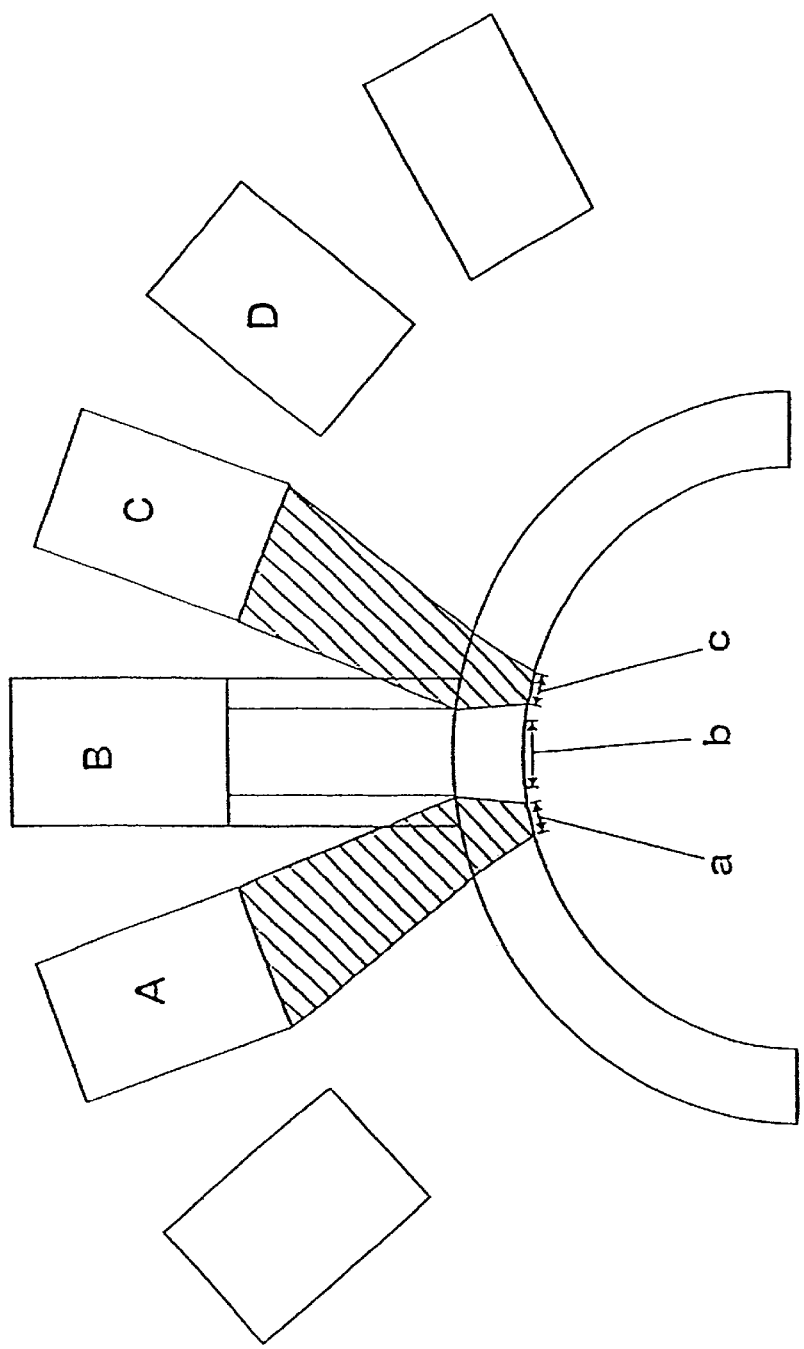
FIG. 2 is a schematic drawing showing a portion of a reflected ultrasonic signal emitted from measuring head B which is received by adjacent measuring heads A and C, according to the invention.

The ultrasonic measuring heads A, B, C, D are operated cyclically. If the ultrasonic measuring head B is operated to transmit an ultrasonic signal, only a portion of the emitted signal, namely the unscattered reflected part is received by its receiver. This part of the signal is shown hatched in FIG. 1. Only a zone b of the tube inner wall 1 is therefore covered directly by the measuring head B. The remainder is scattered on the tube 1 and reflected to the sides. The receivers of the adjacent measuring heads A, C receive a part of these scattered reflected signals. These components of the signal are shown hatched in FIG. 2. These signals correspond to zones a and c on the tube inner wall. As FIG. 2 shows, uncovered zones are left between a and b on the one hand and b and c on the other. However, these uncovered zones are covered by the measuring head C during the transmission of an ultrasonic signal.

Figure 3:
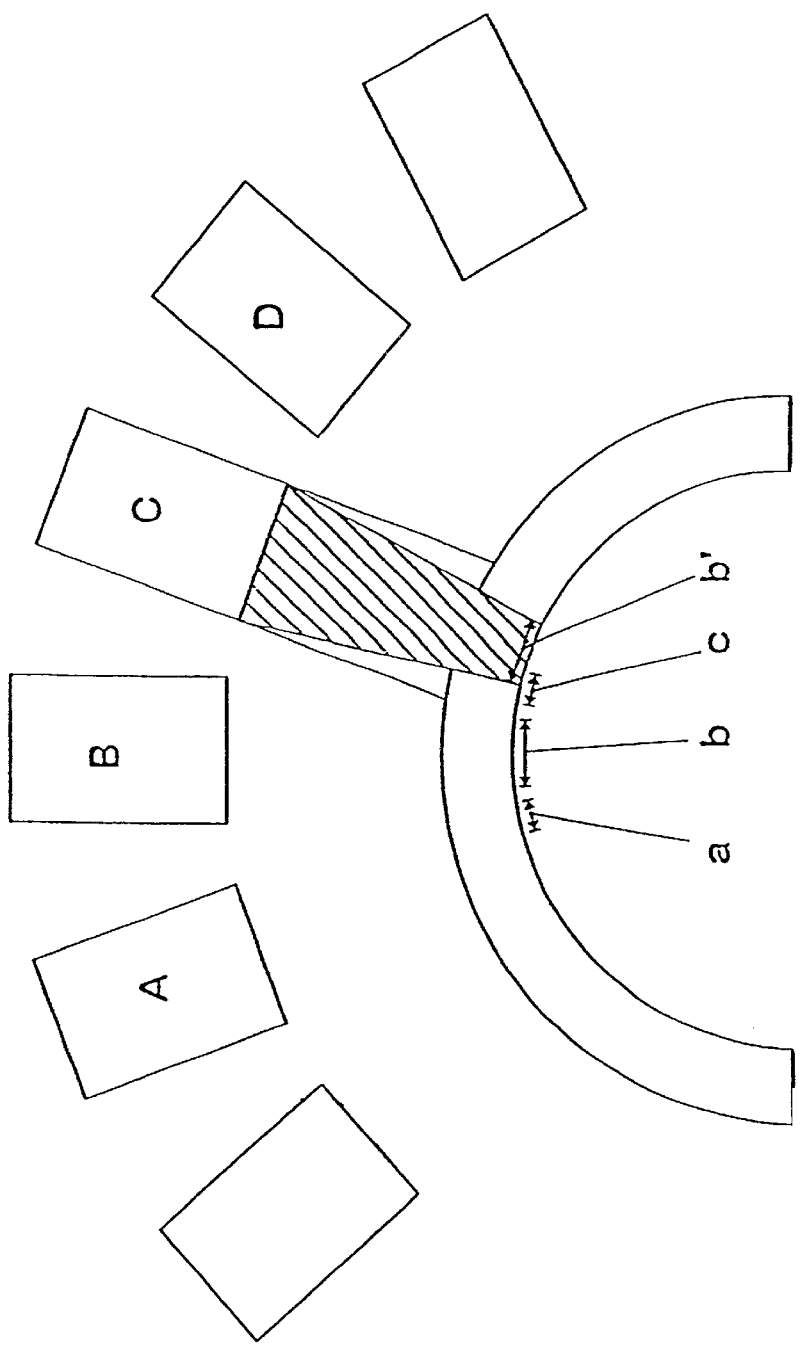
FIG. 3 is a schematic drawing showing a portion of a reflected ultrasonic signal emitted from measuring head C which is received by measuring head C, according to the invention.

As FIG. 3 shows, a zone b' on the tube inner wall is covered by the unscattered reflected signal emitted by the transmitter of the ultrasonic measuring head C.

Figure 4:
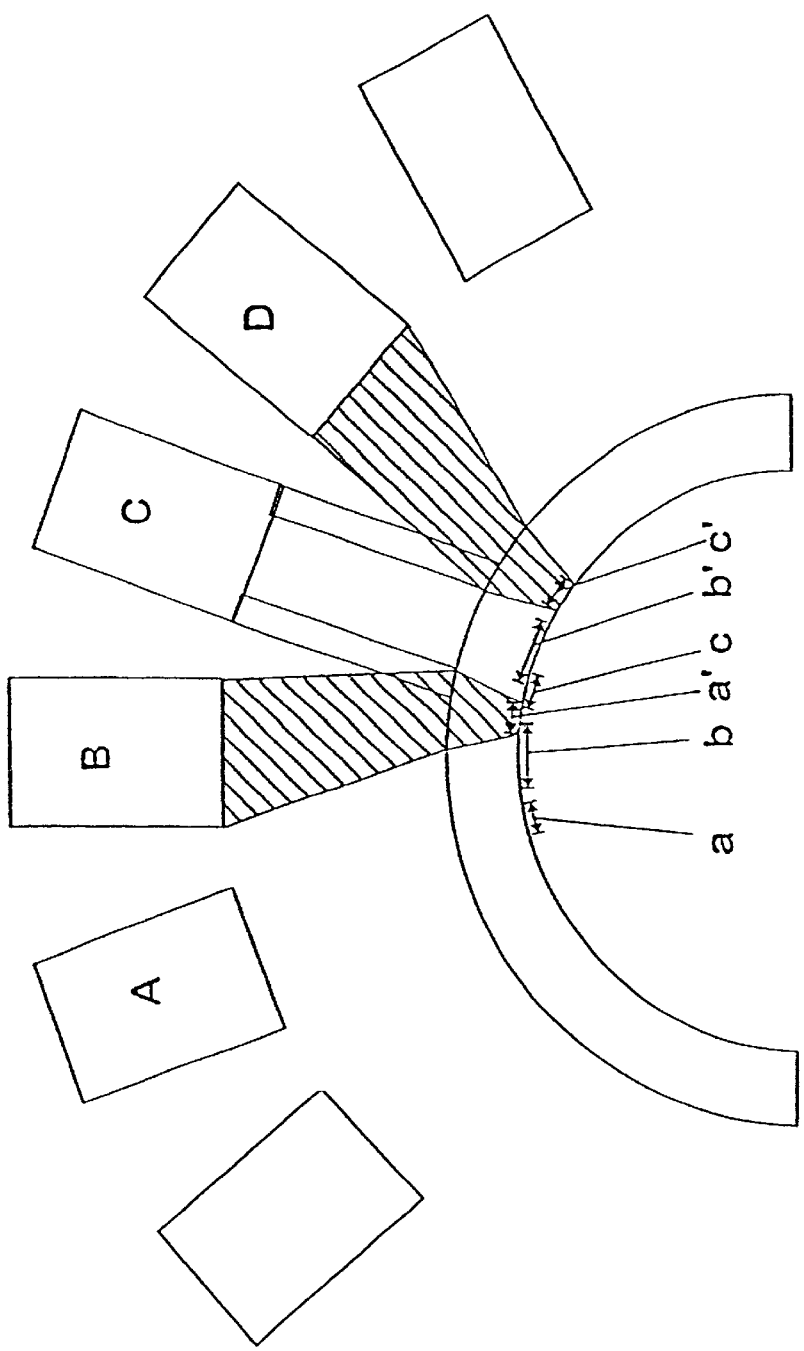
FIG. 4 is a schematic drawing showing a portion of a reflected ultrasonic signal emitted from measuring head C which is received by adjacent measuring heads B and D, according to the invention.

As FIG. 4 shows, the scattered reflected signals of the ultrasonic signal emitted by the transmitter of the ultrasonic measuring head C cover the zones a', c' on the tube inner wall. The zone a' therefore covers the gap between the zones b and c which were not covered by the signal emitted by the transmitter of the ultrasonic measuring head B.

Using the device according to the invention, therefore, it is possible to cover a tube completely using a comparatively small number of measuring heads A, B, C, D for the transmission of ultrasonic signals, also making use of the ultrasonic signal reflected and broken off to the side on the curved surface of the object to be measured. The small number of measuring heads enables the operation to be performed cyclically with a high frequency of measuring sequence, to obtain a complete coverage of the object to be measured in the longitudinal direction also. It is true that measurements can be carried out without any overlapping of the ultrasonic signals reflected with and without scatter, in order to manage with as few ultrasonic measuring heads as possible, but the wall of the object to the measured can also be investigated both by ultrasonic signals reflected without scatter and also by ultrasonic signals reflected by scatter. The latter has the additional effect that due to the different angle of incidence of the refracted ultrasonic signals faults can also be detected which would otherwise be difficult to detect.

What is claimed is:

1. A device for detecting faults in and/or measuring the wall thickness of a continuously moving plastic body by means of ultrasonic signals, said device comprising:

a plurality of measuring heads (A, B, C, D) from which said ultrasonic signals are perpendicularly introduced into said plastic body by means of an ultrasonic transmitter, said measuring heads being distributed one beside the other adjacent to said plastic body and transversely to the direction of motion of said plastic body, and said measuring heads including at least one receiving surface thereon comprising a plurality of measuring zones;

said plastic body having a convexly curved surface, where said surface contains overlapping, predetermined surface zones;

said measuring heads (A, B, C, D) being disposed relative to said plastic body to allow for the sonic propagation, scatter and refraction of said ultrasonic signals on said convexly curved surface of said plastic body, where reflected signals of said ultrasonic signals emitted by one of said measuring heads (B) are received by said emitting measuring head (B) and by said measuring heads (A, C) adjacent on both sides of said emitting measuring head (B);

said signals emitted from said measuring heads (A, C) adjacent on both sides of said measuring head (B) being received by said measuring head (B) from reflected signals emanating from said predetermined surface zones associated with said measuring heads (A, B, C);

said reflected signals being received by said measuring heads and supplied to an evaluation unit;

wherein the number of said adjacent measuring heads (A, C) is $$N \geq \frac{\pi R}{S \tan \alpha},$$

the diameter of said at least one receiving surface of each measuring head is $$K \geq \frac{2\pi R}{NT},$$

and the wavelength of said ultrasonic signals is $$\lambda \geq R\left(1 - \cos\frac{360}{NT}\right),$$

wherein

N=number of measuring heads;
R=external radius of curvature of said convexly curved surface of said plastic body;
S=distance of said measuring heads from said convexly curved surface of said plastic body;
α=opening angle of said ultrasonic transmitter of said measuring heads;
K=diameter of said at least one receiving surface of each of said measuring heads;
T=number of measuring zones per measuring head; and
λ=wavelength of said ultrasonic signal.

* * * * *